United States Patent
Schmidt et al.

(10) Patent No.: US 10,849,567 B2
(45) Date of Patent: Dec. 1, 2020

(54) INDICATION OF RISK FOR CORONARY ARTERY DISEASE

(71) Applicant: ACARIX AS, Kgs Lyngby (DK)

(72) Inventors: Samuel Emil Schmidt, Aalborg SØ (DK); Johannes Jan Struijk, Terndrup (DK)

(73) Assignee: ACARIX AS, Kgs Lyngby (DK)

( * ) Notice: Subject to any disclaimer, the term of this patent is extended or adjusted under 35 U.S.C. 154(b) by 0 days.

(21) Appl. No.: 15/551,356

(22) PCT Filed: Apr. 8, 2016

(86) PCT No.: PCT/EP2016/057798
§ 371 (c)(1),
(2) Date: Aug. 16, 2017

(87) PCT Pub. No.: WO2016/162503
PCT Pub. Date: Oct. 13, 2016

(65) Prior Publication Data
US 2018/0020987 A1    Jan. 25, 2018

(30) Foreign Application Priority Data
Apr. 9, 2015 (EP) .................................. 15163018

(51) Int. Cl.
*A61B 5/02* (2006.01)
*A61B 5/024* (2006.01)
(Continued)

(52) U.S. Cl.
CPC ........ *A61B 5/7275* (2013.01); *A61B 5/02444* (2013.01); *A61B 5/721* (2013.01);
(Continued)

(58) Field of Classification Search
CPC .... A61B 5/02; A61B 7/00; A61B 7/04; A61B 5/02007; A61B 2562/14; A61B 2562/168
(Continued)

(56) References Cited

U.S. PATENT DOCUMENTS 5,109,863 A    5/1992   Semmlow et al.
5,503,161 A *  4/1996   Van Den Heuvel ... A61B 5/145
                                                        128/925
(Continued)

FOREIGN PATENT DOCUMENTS

EP     1103216 A2    5/2001
EP     2014234 A1    1/2009
(Continued)

OTHER PUBLICATIONS

Patel, Samir B. et al, "An adaptive noise reduction stethoscope for auscultation in high noise environments," May 1998, Journal of Acoustical Society of America; NY; vol. 103, No. 5, pp. 2483-2491.
(Continued)

*Primary Examiner* — Jon Eric C Morales
(74) *Attorney, Agent, or Firm* — Schott, P.C.

(57) ABSTRACT

A way of indicating a risk for coronary artery disease is disclosed. A first plurality of first sound recordings of heartbeats and second plurality of second sound recording of the ambient background are obtained. A filtering of each first sound recording is performed by using a simultaneously recorded second sound recording. The filtering of each first sound recording involves determining a diastolic period of the heartbeat of the first sound recording, and performing an adaptive filtering of the first sound recording based in the diastolic period of the first sound recording and the simultaneously recorded second sound recording. This is followed by determination of an indication of the risk for coronary artery disease based on the filtered first sound recordings.

12 Claims, 5 Drawing Sheets

(51) Int. Cl.
  *A61B 7/04* (2006.01)
  *A61B 5/00* (2006.01)
  *A61B 7/02* (2006.01)
  *G16H 50/30* (2018.01)
  *G16H 40/63* (2018.01)
  *A61B 5/0456* (2006.01)

(52) U.S. Cl.
  CPC .......... *A61B 5/7203* (2013.01); *A61B 5/7235* (2013.01); *A61B 5/7246* (2013.01); *A61B 5/7278* (2013.01); *A61B 7/026* (2013.01); *A61B 7/04* (2013.01); *G16H 40/63* (2018.01); *G16H 50/30* (2018.01); *A61B 5/0456* (2013.01); *A61B 2562/0204* (2013.01)

(58) Field of Classification Search
  USPC ....................................................... 600/528
  See application file for complete search history.

(56) References Cited

U.S. PATENT DOCUMENTS

| | | |
|---|---|---|
| 6,520,918 B1 | 2/2003 | Stergiopoulos et al. |
| 6,805,671 B2 | 10/2004 | Stergiopoulos et al. |
| 7,458,939 B2 | 12/2008 | Munk |
| 7,953,230 B2 | 5/2011 | Nadjar et al. |
| 2010/0094152 A1* | 4/2010 | Semmlow ................ A61B 7/00 600/528 |
| 2013/0211291 A1 | 8/2013 | Tran |
| 2014/0180153 A1 | 6/2014 | Zia et al. |

FOREIGN PATENT DOCUMENTS

| | | |
|---|---|---|
| EP | 2471461 | 4/2012 |
| WO | 1997047236 A1 | 12/1997 |
| WO | 2002032313 A2 | 4/2002 |
| WO | 2003079891 A2 | 10/2003 |
| WO | 2008000254 A1 | 1/2008 |
| WO | 2009138932 A1 | 11/2009 |
| WO | 2012080209 A1 | 6/2012 |

OTHER PUBLICATIONS

Yasemin M. Akay et al., "Noninvasive Acoustical Detection of Coronary Artery Disease: A Comparative Study of Signal Processing Methods", Transactions on Biomedical Engineering, pp. 571-578, Jun. 1993.

* cited by examiner

INDICATION OF RISK FOR CORONARY ARTERY DISEASE

TECHNICAL FIELD

The present invention relates to the indicating of the risk of coronary artery disease, and in particular to methods and systems configured to indicate a risk of coronary artery disease from measured acoustic signals.

BACKGROUND

Coronary Artery Disease (CAD) is a condition in which plaque builds up inside the coronary arteries. These arteries supply the heart muscle with oxygen-rich blood. Plaque narrows the arteries and reduces blood flow to the heart, which may cause angina or a heart attack. Over time, CAD may weaken the heart muscle and lead to heart failure and arrhythmias. CAD is one of the most common types of heart disease, and efficient and accurate tools for estimating or indicating the risk of CAD are therefore important.

Historically, detection of CAD has involved patient history, physical examination, stress testing, and possibly analysis of coronary angiograms. During physical examination, a stethoscope is often used to examine the sound of the heart. Although the role of the stethoscope in the modern clinic seems to be fading, new electronic stethoscopes with integrated diagnostic algorithms may alter the trend and expand the clinical potential of the stethoscope. There is therefore a need for developing efficient and accurate diagnostic algorithms for estimating a risk for CAD.

A number of distinct heart sounds are generated during a heartbeat. The sounds are produced by blood turbulence and vibration of cardiac structures, primarily due to the closing of the valves within the heart. Four sounds can typically be identified, which are commonly called S1, S2, S3 and S4.

The S1 sound is usually the loudest heart sound and is the first heart sound during ventricular contraction. S1 is often described as a "lubb" sound. S1 occurs at the beginning of ventricular systole and relates to the closure of atrioventicular valves between the atria and the ventricles.

The S2 sound is often described as a "dubb" sound. S2 occurs at the beginning of the diastole and relates to the closing of the semilunar valves separating the aorta and pulmonary artery from the left and right ventricles, respectively. S1 and S2 sounds are "normal heart sounds" that can easily be heard with a stethoscope.

However, the S3 and S4 sounds can usually not be heard in the normal heart of a person over 40 years old. These are typically attributed "abnormal heart sounds". The S3 sound, also referred to as "ventricular gallop", occurs in the early diastolic period and is caused by the ventricular wall distending to the point it reaches its elastic limit. The S4 sound, also referred to as "atrial gallop", occurs near the end of atrial contraction and is also caused by the ventricular wall distending until it reaches its elastic limit.

Heart sounds can be used to augment the diagnosis and to help assess the severity of important types of a cardiac disease. For example, after age 40, S3 can indicate congestive heart failure, and S4 can indicate hypertension, acute myocardial infarction, or CAD. Unfortunately, studies have shown that even highly experienced physicians do not reliably detect important heart sounds. Therefore various diagnostic tools have been developed to support physicians in detecting possible heart diseases. For example, such tools are described in WO 2008/000254 A1 and WO 2012/080209 A1.

There is a problem with existing electronic stethoscopes using algorithms to detect or estimate the risk of CAD. The CAD related murmurs are weak and the difference between CAD and non-CAD sounds are typically small and hard to detect. The algorithms used are likely to be sensitive to other types of noise, such as ambient noise and physiological noise originating from a patient. This limits the usability of the electronic stethoscopes, since the environment has to be controlled to avoid ambient noise. Ambient noise may be hard to control and the practical use of an electronic stethoscope, in particular a portable electronic stethoscope, is therefore limited. There is a need for reducing the sensitivity of electronic stethoscopes, in particular those for estimating the risk for CAD, to ambient noise. There is also a need for improving the efficiency and accuracy when determining or classifying the risk for CAD.

It is therefore an object to address some of the problems and technical challenges outlined above.

SUMMARY

According to a first aspect, the above object is achieved by a method for indicating a risk for coronary artery disease for a person. The method comprises: (a) obtaining a first plurality of first sound recordings, wherein each first recording is of a heartbeat of the person, and (b) obtaining a second plurality of second sound recording, wherein each second sound recording is of the ambient background surrounding the person and being recorded simultaneously to a first sound recording of the first plurality. The method further comprises: (c) performing a filtering of each first sound recording of the first plurality by using a simultaneously recorded second sound recording of the second plurality. The filtering of each first sound recording comprises: (i) determining a diastolic period of the heartbeat of the first sound recording, and (ii) performing an adaptive filtering of the first sound recording for reducing noise originating from the ambient background that is present in the first sound recording and in the simultaneously recorded second sound recording. The adaptive filtering is based on a first portion of the first sound recording and on a second portion of the simultaneously recorded second sound recording, and wherein the first portion and the second portion are covered by the diastolic period. The method further comprises: (d) determining an indication of the risk for coronary artery disease based on the filtered first sound recordings of the first plurality.

Alternatively, in performing the filtering (c), the second step (ii) of performing an adaptive filtering may be replaced by: (ii) determining a first portion of the first sound recording and a second portion of the simultaneously recorded second sound recording, wherein the first portion and the second portion are covered by the diastolic period. In this alternative, the performing the filtering (c) continues with: (iii) determining an adaptive filter for the first sound recording, wherein the adaptive filter is based on the first portion and the second portion and configured for reducing noise originating from the ambient background that is present in both the first sound recording and in the simultaneously recorded second sound recording, and (iv) employing the adaptive filter to the first sound recording.

Covered by the diastolic period is here understood to encompass the first portion and the second portion corresponding in extent to the diastolic period, or the first portion and the second portion being located within the diastolic period. The first portion and the second portion may be of equal length. The first portion and the second portion may be concurrent, or correspond to the same period in time. Throughout these specifications, each individual occurrence of sound level may be understood as the power or the amplitude, such as the power or amplitude of the first sound recording or the second sound recording.

Noise in a first sound recording that originates from the ambient background typically has traveled through the chest of the person, which may cause a time delay and a frequency shift of the noise with respect to the noise in the corresponding second sound recording.

The overall effect of the adaptive filter or filtering is that the effect of ambient noise on the indication of the risk for CAD is reduced or removed, which gives a more robust and accurate result. Further, the adaptive filtering allows for an optimization with respect to the noise reduction or removal. Large variations in sounds levels may cause artifacts in an adaptive filter. By letting the first portion and the second portion to be covered by the diastolic period, the strong S1 and S2 sounds are excluded when forming the adaptive filter, thus enabling weaker CAD related heart sounds to be detected, which leads to an improved accuracy in determining the indication of a risk for CAD.

Subtracting ambient sounds recorded in the second sound recordings directly from heart sounds in the first sound recording would introduce errors, since the noise in the heart sounds corresponding to the ambient sounds are delayed and have an altered frequency distribution due to passage through the chest. Thus, the adaptive filtering will improve the accuracy of the determining of the indication of the risk for CAD.

The transfer function of the chest of a person varies with time. By limiting the time interval of the first and second periods as described above, the transfer function can be assumed to be time-invariable, which allows for a more accurate modeling of the chest and a more accurate adaptive filter.

One alternative way to avoid noise is to remove the first sound recordings that are noisy. The adaptive filter allows for the noise of the first sound recordings to be reduced or removed in an efficient and accurate manner, which means that more first sound recordings can be used in the determining of the indication of the risk for CAD. In a noisy environment, less first sound recordings are required for determining the risk of CAD, and quicker indication of CAD is achieved.

According to a second aspect, the above object is achieved by: a system for indicating a risk for coronary artery disease for a person, wherein the system comprises: (A) a first acoustic sensor configured to be placed on the chest of the person and for recording heartbeats, and (B) a second acoustic sensor configured to be placed at the person and for recording ambient background sounds. The system further comprises: (C) a processor operatively connected with the first acoustic sensor and the second acoustic sensor. The processor is configured to: (a) obtain a first plurality of first sound recordings with the first acoustic sensor, wherein each first recording is of a heartbeat of the person, and (b) obtain a second plurality of second sound recording with the second acoustic sensor, wherein each second sound recording is of the ambient background surrounding the person and being recorded simultaneously to a first sound recording of the first plurality. The processor is further configured to: (c) perform a filtering of each first sound recording of the first plurality by using a simultaneously recorded second sound recording of the second plurality. The filtering of each first sound recording comprises: (i) determining a diastolic period of the heartbeat of the first sound recording, and (ii) performing an adaptive filtering of the first sound recording for reducing noise originating from the ambient background that is present in both the first sound recording and in the simultaneously recorded second sound recording. The adaptive filtering is based on a first portion of the first sound recording and on a second portion of the simultaneously recorded second sound recording, and wherein the first portion and the second portion are covered by the diastolic period. The processor is further configured to: (d) determining an indication of the risk for coronary artery disease based on the filtered first sound recordings of the first plurality.

Alternatively, in the filtering (c) of each first sound recording. the second step (ii) of performing an adaptive filtering may be replaced by: (ii) determining a first portion of the first sound recording and a second portion of the simultaneously recorded second sound recording, wherein the first portion and the second portion are covered by the diastolic period. The filtering (c) then continues with: (iii) determining an adaptive filter for the first sound recording, wherein the adaptive filter is based on the first portion and the second portion and configured for reducing noise originating from the ambient background that is present in both the first sound recording and in the simultaneously recorded second sound recording, and (iv) employing the adaptive filter to the first sound recording.

A processor is here understood to encompass a processor that is dedicated for the described function. Alternatively, the processor may be a general purpose processor. A processor is here understood to also encompass a single processor that individually handles a process, or a group of processors that cooperate to handle a process. The processor may encompass a transient memory for performing its function or running the program code instructions. The system may be portable electronic stethoscope.

The effects and advantages described in relation to the first aspect are also true for the system according to the second aspect.

According to a third aspect, the above object is achieved by a computer program product for being used in a system comprising: (A) a first acoustic sensor configured to be placed on the chest of the person and for recording heartbeats, (B) a second acoustic sensor configured to be placed at the person and for recording ambient background sounds, and (C) a processor operatively connected with the first acoustic sensor and the second acoustic sensor. The computer program product comprises program code instructions configured to, when executed by the processor of the system, cause the processor to: (a) obtain a first plurality of first sound recordings with the first acoustic sensor, wherein each first recording is of a heartbeat of the person, and (b) obtain a second plurality of second sound recording with the second acoustic sensor, wherein each second sound recording is of the ambient background surrounding the person and being recorded simultaneously to a first sound recording of the first plurality. The computer program product further comprises program code instructions configured to: (c) perform a filtering of each first sound recording of the first plurality by using a simultaneously recorded second sound recording of the second plurality. The filtering of each first sound recording comprises: (i) determining a diastolic period of the heartbeat of the first sound recording, and (ii) performing an adaptive filtering of the first sound recording for reducing noise originating from the ambient background that is present in both the first sound recording and in the simultaneously recorded second sound recording. The adaptive filtering is based on a first portion of the first sound recording and on a second portion of the simultaneously recorded second sound recording, and wherein the first portion and the second portion are covered by the diastolic period. The computer program product further comprises program code instructions configured to: (d) determine an indication of the risk for coronary artery disease based on the filtered first sound recordings of the first plurality.

The effects and advantages described in relation to the first aspect are also true for the computer program product according to the third aspect.

According to a fourth aspect, the above object is achieved by a method for filtering a first sound recording of a heartbeat of a person by using a second sound recording of the ambient background surrounding the person. The second sound recording is recorded simultaneously to the first sound recording, and the method comprises: (i) determining a diastolic period of the heartbeat of the first sound recording. The method further comprises, (ii) performing an adaptive filtering of the first sound recording for reducing noise originating from the ambient background that is present in the first sound recording and in the second sound recording. The adaptive filtering is based on a first portion of the first sound recording and on a second portion of the second sound recording, and the first portion and the second portion are covered by the diastolic period.

As for the first aspect, the overall effect of the adaptive filtering is that the effect of ambient noise is reduced or removed. The adaptive filtering allows for an optimization with respect to the noise reduction or removal. Large variations in sound levels may cause artifacts in an adaptive filter. By letting the first portion and the second portion to be covered by the diastolic period, the strong S1 and S2 sounds are excluded when forming the adaptive filter, thus enabling weaker heart sounds to be detected. As mentioned above, the transfer function of the chest of a person varies with time. By limiting the time interval of the first and second portions, the transfer function can be assumed to be time-invariable, which allows for a more accurate modeling of the chest and a more accurate adaptive filter.

According to a fifth aspect, the above object is achieved by an electronic stethoscope comprising: (A) a first acoustic sensor configured to be placed on the chest of a person and for recording heartbeats, and (B) a second acoustic sensor configured to be placed at the person and for recording ambient background sounds. The electronic stethoscope further comprises: (C) a processor operatively connected with the first acoustic sensor and the second acoustic sensor. The processor is configured to: (a) obtain a first sound recordings with the first acoustic sensor, wherein the first recording is of a heartbeat of the person, and (b) obtain a second sound recording with the second acoustic sensor, wherein the second sound recording is of the ambient background surrounding the person and being recorded simultaneously to a first sound recording of the first plurality. The processor is further configured to: (c) perform a filtering of the first sound recording by using the simultaneously recorded second sound. The filtering comprises: (i) determining a diastolic period of the heartbeat of the first sound recording, and (ii) performing an adaptive filtering of the first sound recording for reducing noise originating from the ambient background that is present in both the first sound recording and in the simultaneously recorded second sound recording. The adaptive filtering is based on a first portion of the first sound recording and on a second portion of the simultaneously recorded second sound recording, and wherein the first portion and the second portion are covered by the diastolic period.

The effects and advantages described in relation to the fourth aspect are also true for the electronic stethoscope according to the fifth aspect.

In the third to fifth aspects, the second step (ii) of performing an adaptive filtering may be replaced by: (ii) determining a first portion of the first sound recording and a second portion of the simultaneously recorded second sound recording, wherein the first portion and the second portion are covered by the diastolic period, (iii) determining an adaptive filter for the first sound recording, wherein the adaptive filter is based on the first portion and the second portion and configured for reducing noise originating from the ambient background that is present in both the first sound recording and in the simultaneously recorded second sound recording, and (iv) employing the adaptive filter to the first sound recording.

Additional or alternative features of the above aspects are explained in the detailed description below or in the appended claims. Further objects may also be construed from the detailed description.

DETAILED DESCRIPTION

In the different aspects of the invention, step (d) of determining an indication may comprise: (d1) determining one or more first heart sound levels from the filtered first sound recordings, wherein each first heart sound level is determined from a first period within a filtered first sound recording, and (d2) determining the risk for coronary artery disease based on the one or more first heart sound levels. The first period may correspond to the diastolic period, or a period within the diastolic period, or the first portion of the first sound recording, or a portion within the first portion.

The step (d) of determining an indication of the risk for coronary artery disease based on the filtered first sound recordings of the first plurality may comprise: performing one of the methods described in WO 2012/080209 A1 for diagnosing of coronary artery disease with the filtered first sound recordings of the first plurality as the recorded acoustic data.

In the step (ii), the adaptive filtering may be performed on the complete first sound recording, or on a period corresponding to the diastolic period, or on a period within the diastolic period, or on the first portion of the first sound recording, or on a portion within of the first portion, or on the first period.

As described above, there are great variations of the amplitude of a heartbeat sound, which may cause artifacts in the adaptive filtering and reduce the accuracy of when determining the indication of the risk for CAD. The amplitude of the of the sounds that may indicate CAD in the diastolic period may be several orders of magnitude smaller than the "normal heart sounds", such as the S1 and S2 sounds. Thus, the limiting the of first portion to, the second portion, and the first period to the diastolic period, or a period within the diastolic period, synergetically contributes an improved accuracy of the determining the risk of CAD, which in turn gives a more accurate indication of CAD.

The first portion of the first sound recording and the second portion of the simultaneously recorded second sound recording may start between 100 and 200 ms, or at 150 ms, subsequent to the start of the diastolic period. The first portion of the first sound recording and the second portion of the simultaneously recorded second sound recording may have a length that is less than 400 ms, or a length that is less than 300 ms. The step (i) of determining the diastolic period may also comprise determining the onset of the S2 sound, and the first portion of the first sound recording and the simultaneously recorded second portion of the second sound recording may start between 100 and 200 ms, or at 150 ms, subsequent to the onset of the S2 sound. The step (i) of determining the diastolic period may also comprise determining the onset of the S4 sound, and the first portion of the first sound recording and the second portion of the simultaneously recorded second sound recording may end before the onset of the S4 sound. The above limitations of the extent of the first and second portions contribute to avoiding strong heart sounds, which improves the adaptive filtering. If the first period is limited by the first portion, as described above, a more accurate indication of CAD can thus be achieved. The limitations are particularly advantageous if the first period correspond to the first portion, since they allow for a filtered length of first period that is sufficiently long for obtaining a strong signal of the sounds possibly relating to CAD.

In the step (ii), the adaptive filtering may be based on a Wiener filter. This allows for a fast filtering that can be applied to the whole first sound recording. Alternatively or additionally, in the step (ii), the adaptive filtering may be based on a recursive least square adaptive filter, a Least Mean Squares (LMS) adaptive filters, and/or a normalized LMS adaptive filter.

The method according to the first aspect may further comprise prior to the step (c) of performing the filtering: (e) determining a first noise level of each second sound recording of the second plurality, and (f) discarding the first sound recordings having a simultaneously recorded second recording with a first noise level above a first determined noise level. The processor in the second aspect may further be configured to perform the above steps (e) and (f) prior to the step (c). Similarly, the computer program product of the third aspect may comprise program code instructions configured to cause the processor to perform the above steps (e) and (f) prior to the step (c).

In step (e), the first noise level may be based on a variance of the sound level of the complete second sound recording, or at least of a period corresponding to or covering a complete heartbeat in the second sound recording. In step (e), a first band-pass filtering of the complete second sound recording, or at least of a period corresponding to or covering a complete heartbeat in the first sound recording, may be performed prior to determining the first noise level. The first band-pass filtering may allow passage within 60-300 Hz. In step (f), the first determined noise level may be approximately 65 dB.

With the above described treatment of the second sound recordings of the second plurality, first sound recordings that are affected by general background noise that extends over a longer portion or part of a heartbeat, such as an alarm or person speaking, are removed. This, way, the steps (e) and (f) features contribute to a more robust determining of the indication of the risk for CAD.

The method according to the first aspect may further comprise prior to the step (c) of performing the filtering: (g) determining a second heart sound level of each first sound recording of the first plurality, and (h) discarding the first sound recordings having a second heart sound level that is below a first determined heart sound level. The processor in the second aspect may further be configured to perform the above steps (g) and (h) prior to the step (c). Similarly, the computer program product of the third aspect may comprise program code instructions configured to cause the processor to perform the above steps (g) and (h) prior to the step (c).

In step (g), the second heart sound level may be based on a mean or variance of the sound level of the complete first sound recording, or at least of a period corresponding to or covering a complete heartbeat in the first sound recording. In step (g), a second band-pass filtering of the complete first sound recording, or at least of a period corresponding to or covering a complete heartbeat in the first sound recording, may be performed prior to determining the second heart sound level. The second band-pass filtering may allow passage within 60-300 Hz. In step (h), the first determined heart sound level may be approximately 60 dB.

The above described treatment of the first sound recordings of the first plurality may ensure that they have been obtained properly before being used to determine the indication of the risk for CAD. For example, if the first acoustic sensor is not placed in a correct manner on the patient, the heart sound level may be below 60 dB, and the affected first sound recordings are discarded. This contributes to a more robust determining of the indication of the risk for CAD.

The method according to the first aspect may further comprise subsequent to step (c) of performing the filtering and prior to the step (d) of determining an indication: (i) determining a second noise level for a second period of each second sound recording of the second plurality, and (j) discarding each first sound recordings having a simultaneously recorded second recording with a second noise level in the second period above a second determined noise level. The processor in the second aspect may further be configured to perform the above steps (i) and (j) subsequent to step (c) and prior to the step (c). Similarly, the computer program product of the third aspect may comprise program code instructions configured to cause the processor to perform the above steps (i) and (j) subsequent to step (c) and prior to the step (c).

The second period may correspond to the diastolic period, or a period within the diastolic period, or the second portion of the second sound recording. In step (i), the second noise level may be based on a variance of the sound level of the second period. In step (i), a third band-pass filtering may be performed prior to determining the second noise level. The third band-pass filtering may allow passage within 100-1200 Hz. The third band-pass filtering may be performed on the second period. In step (j), the second determined noise level may be approximately 60 dB.

Despite the use of the adaptive filter, and the optional discarding by steps (e) and (f) as described above, some heartbeats may still be contaminated by very intense and brief ambient noise in the diastolic period, like a door closing or an item being dropped. Such ambient noise may be avoided by steps (i) and (j), thus contributing to a more robust and accurate determining of the indication of the risk for CAD.

The method according to the first aspect may further comprise subsequent to step (c) of performing the filtering and prior to the step (d) of determining an indication: (k) determining a third heart sound level for a third period of each first sound recording of the first plurality, and (l) discarding the first sound recording if the third heart sound level exceeds a second determined heart sound level. The processor in the second aspect may further be configured to perform the above steps (k) and (l) subsequent to step (c) and prior to the step (d). Similarly, the computer program product of the third aspect may comprise program code instructions configured to cause the processor to perform the above steps (k) and (l) subsequent to step (c) and prior to the step (d).

The third period may correspond to the diastolic period, or a period within the diastolic period, or the first portion of the first sound recording, or correspond to the second period. In step (k), the third heart sound level may be based on a mean or variance of the sound levels of the third period. In step (k), the third heart sound level may be based on the median of the variance of the sound levels of the third periods. In step (k), a fourth band-pass filtering may be performed prior to determining the third heart sound level. The fourth band-pass filtering may allow passage within 100-1200 Hz. The fourth band-pass filtering may be performed on the third period. In step (l), the determined third heart sound level may be between 0.5 and 6 dB, or approximately 3 dB, greater than the median of the mean or variance of the sound levels of the third periods. The steps (k) and (l) may be performed repeatedly in an iterative process.

In addition to ambient noise, a first sound recording may be contaminated by internal physiological noise, such as bowel or peristaltic sound. Such internal noise may be removed by the steps (k) and (l), which contributes a more robust and accurate determining of the indication of the risk for CAD.

The system of the second aspect or the electronic stethoscope of the fifth aspect may comprise a support for supporting the first acoustic sensor and the second acoustic sensor, and for positioning the second acoustic sensor at the first acoustic sensor. The system may comprise a housing for accommodating the first acoustic sensor and the second acoustic sensor. The housing may be configured to acoustically shield the first acoustic sensor from the ambient background.

The program code instructions of the third aspect may be stored on a non-transitory memory.

The aspects described above in the summary and detailed description are to be read together with the claims and may further encompass any of the features described in the claims.

DETAILED DESCRIPTION OF DRAWINGS

The following detailed description refers to the accompanying drawings. The same reference numbers in different drawings identify the same or similar elements, steps, or features. Further, the following detailed description is provided for the purpose of illustration and explanation of some example embodiments.

Figure 1:
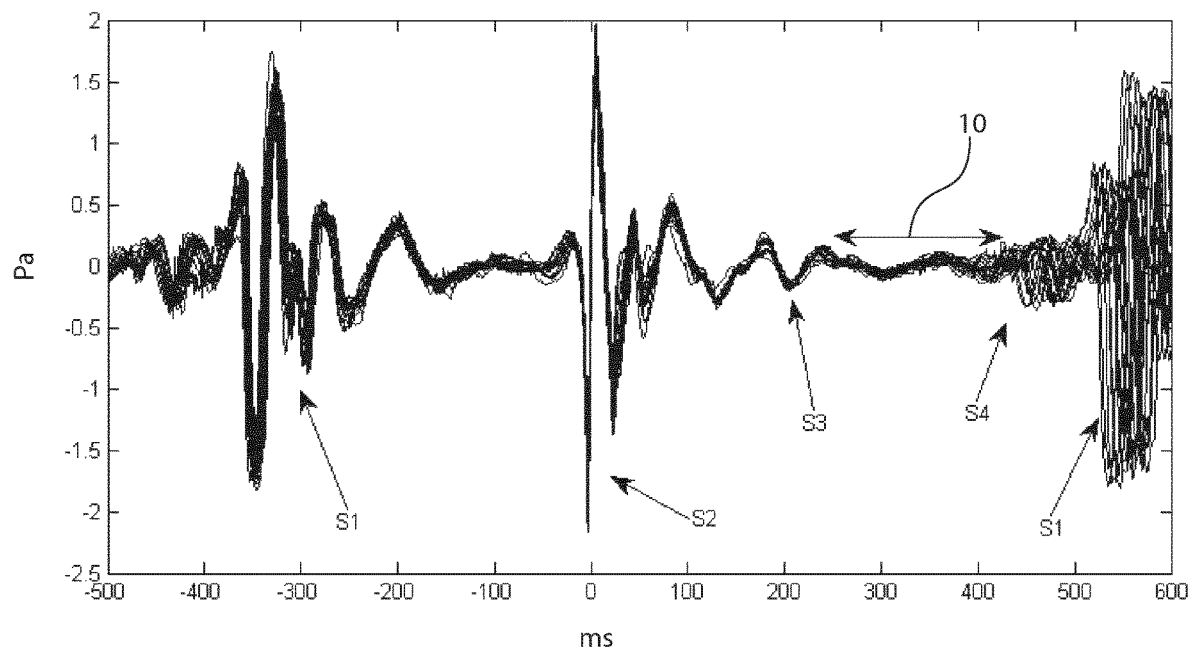
FIG. 1 is a plot of several overlaid recorded heartbeats,
FIG. 2 schematically illustrates an embodiment of a system.

FIG. 1 is a plot of several overlaid recorded heartbeats. The S1, S2, S3, and S4 sounds are indicated, as well as the diastasis or diastolic period 10. The heartbeats have been aligned with respect to their respective S2 sound. The horizontal axis indicates the time in milliseconds with respect to the onset of the S2 sound. The vertical axis indicates the sound pressure in Pascal.

Figure 2:
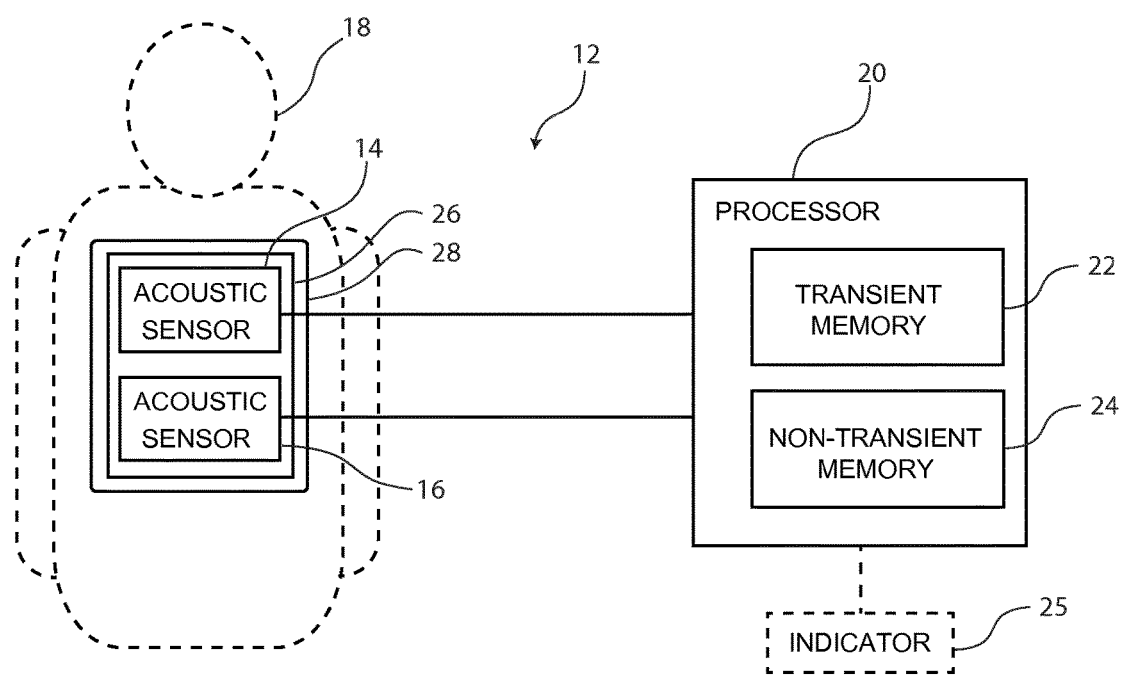

FIG. 2 schematically illustrates an embodiment of a system 12 for indicating a risk for CAD for a person. The system 12 has a first acoustic sensor 14 that can be placed on the chest of a person 18 and record heartbeats. The system 12 also has a second acoustic sensor 16 that can be placed at the person 18 and record ambient background sounds. A processor 20 is connected with the first acoustic sensor 14 and the second acoustic sensor 16. The processor 20 has a transient memory 22 which can store recordings from the first acoustic sensor 14 and the second acoustic sensor, and by which it can execute program code instructions.

The system 12 comprises a support 26 that supports the first acoustic sensor 14 and the second acoustic sensor 16 and positions the second acoustic sensor 16 at the first acoustic sensor 14. The system 12 further has a housing 28 that accommodates the first acoustic sensor 14 and the second acoustic sensor 16. The system 10 also has a non-transient memory 24 storing program code instructions for the processor.

One application of the above system is as an electronic stethoscope. In a variant of the embodiment, the program code instructions cause the processor to perform a method for indicating the risk for CAD. Several embodiments of such methods, or related methods, are described below.

In one embodiment of the system, it additionally has an indicator 25 operatively connected with the processor 30. The indicator 25 can, for example, have a set of differently colored lamps or a display that shows the determined indication. The indication as such may be color coded or represented by a number that can be associated with the risk for CAD.

Figure 3:
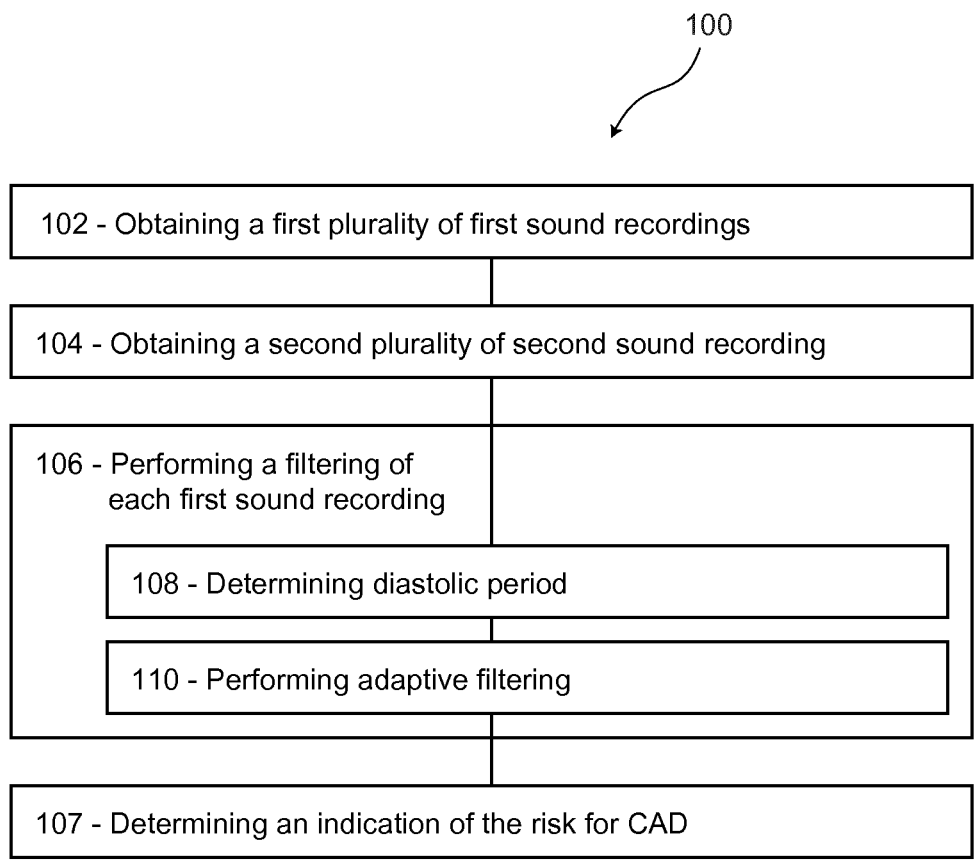
FIG. 3 is a flow chart schematically illustrating an embodiment of a general method.

FIG. 3 is a flow chart schematically illustrating an embodiment of a general method 100 for indicating a risk for CAD for a person. A first plurality of first sound recordings is obtained 102, where each of the first recordings is of a heartbeat of the person. A second plurality of second sound recording is also obtained 104, where each second sound recording is of the ambient background surrounding the person and is recorded simultaneously to a first sound recording of the first plurality. This means that each second sound recording forms a pair with a first sound recording.

Subsequently, a filtering of each first sound recording of the first plurality is performed 106. The filtering is adaptive and uses a simultaneously recorded second sound recording. In the filtering 106 of each first sound recording, a diastolic period of the heartbeat of the first sound recording is first determined 108. An adaptive filtering of the first sound recording is then performed 110. The adaptive filtering is configured to reduce noise originating from the ambient background that is present in both the first sound recording and in the simultaneously recorded second sound recording.

The adaptive filtering 110 is based on, or generated from, a first portion of the first sound recording and on a second portion of the simultaneously recorded second sound recording, where the first portion and the second portion are covered by and located within the diastolic period.

Subsequent to the filtering 106, an indication of the risk CAD is determined 107 based on the filtered first sound recordings of the first plurality.

Figure 8:
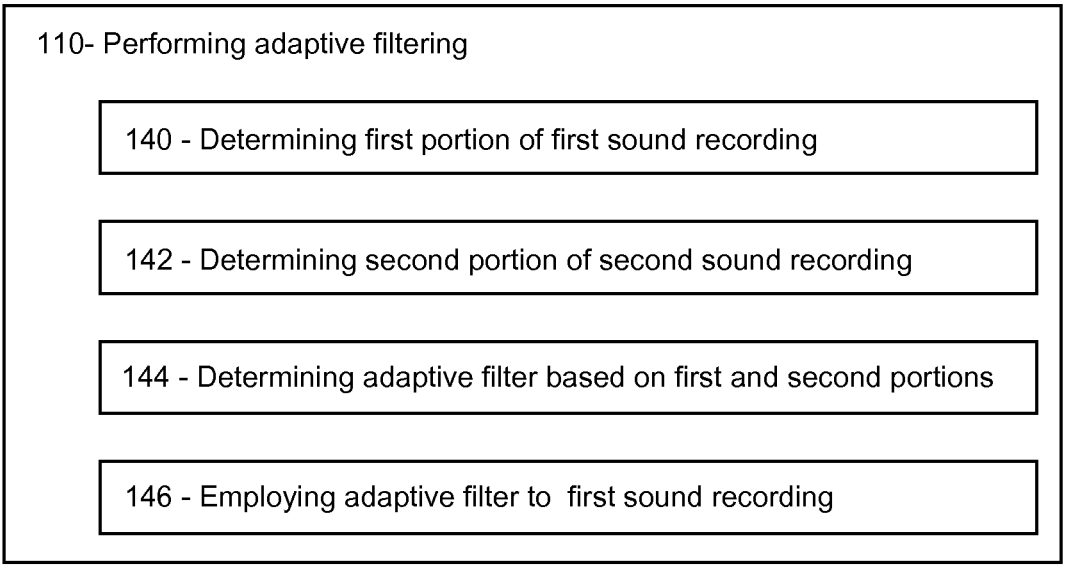
FIG. 8 is a flow chart illustrating a detailed embodiment of an adaptive filtering.

A flow chart illustrating a detailed embodiment of the adaptive filtering 110 is shown in FIG. 8. First, a first portion of the first sound recording is determined 140 and a second portion of the simultaneously recorded second sound recording is determined 142. The adaptive filter is then determined 146 based on the first portion and the second portion so that it can reduce noise originating from the ambient background that is present in both the first and second sound recordings. Subsequently, a portion of the first sound recording, e.g. the first portion, is filtered 146 by the adaptive filter.

Figure 4:
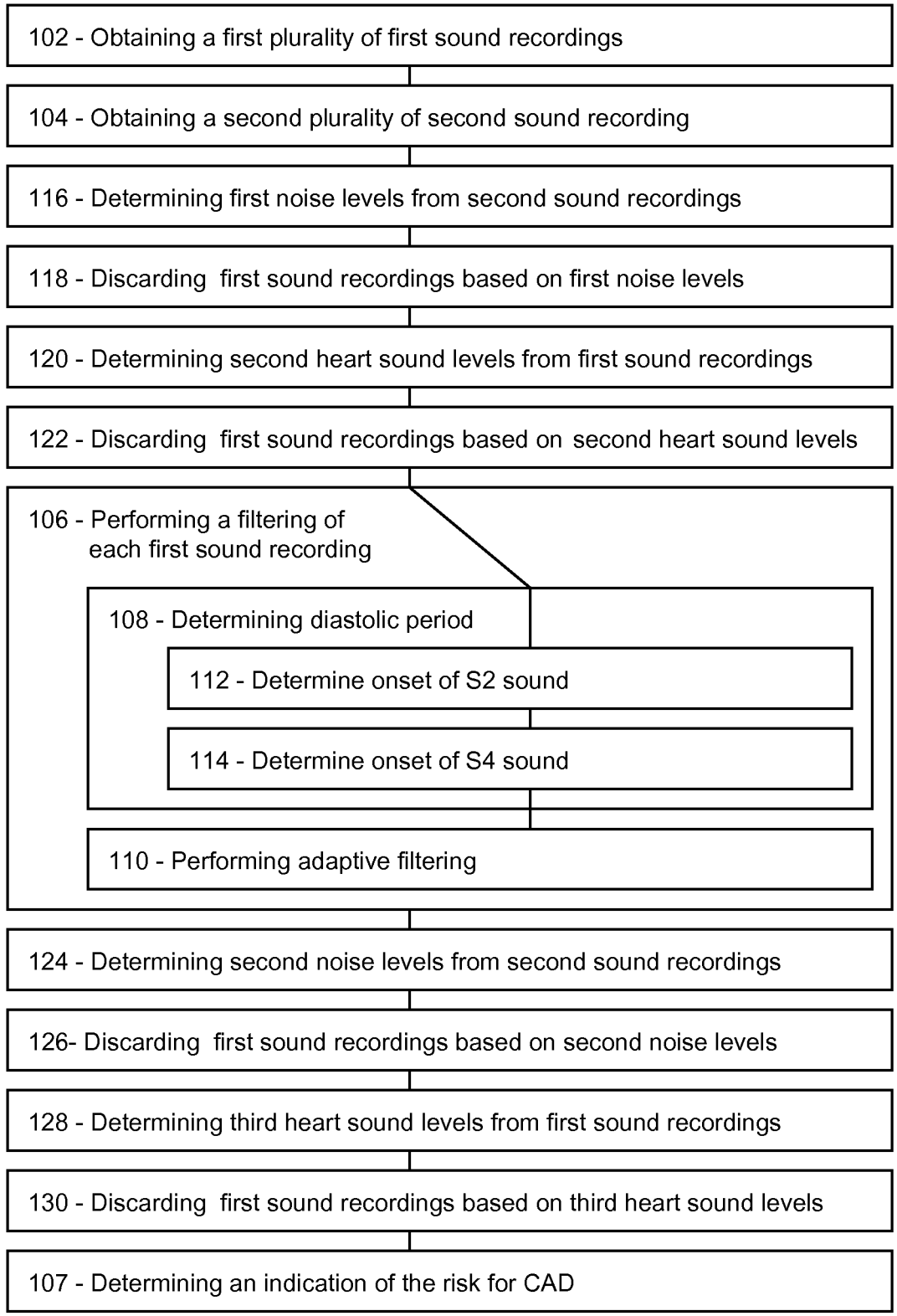
FIG. 4 is a flow chart illustrating a detailed embodiment of a method.

FIG. 4 is a flow chart illustrating a detailed embodiment of a method 100 for indicating a risk for CAD of a person. The steps described in relation to FIG. 3 are included and indicated with the same indexing.

For each first portion of the first sound recording and the second portion of the simultaneously recorded second sound recording, the first portion and the second portion are of equal length, and the first portion and the second portion are concurrent. The first portion of the first sound recording and the second portion of the simultaneously recorded second sound recording start 150 ms after to the start of the diastolic period. Further, the length of the first portion of the first sound recording and the second portion of the simultaneously recorded second sound have a length that is no longer than 300 ms.

When determining 108 the diastolic period the onset of the S2 sound is determined 112. For example, this can be done as described by Schmidt et al. (Physiol. Meas. 31 (2010) 513-529). The first portion of the first sound recording and the second portion of the simultaneously recorded second sound recording start at 150 ms subsequent to the onset of the S2 sound.

Additionally, the onset of the S4 sound is also determined 114. For example, this can be done by aligning heartbeats according to their respective S1 sounds. The S4 sound is linked to the S1 sound, which means that the S4 sound is typically aligned with the S1 sound. The activity before the S4 sound is regarded as related to the previous heartbeat. The onset of the S4 sound is regarded as the time at which the heartbeats start to be synchronized according to an alignment of the subsequent S1 sounds. Further, the first portion of the first sound recording and the second portion of the simultaneously recorded second sound recording end before the onset of the S4 sound. However, the abovementioned length of 300 ms may cause the first and second periods to end earlier than the onset of the S4 sound.

The adaptive filtering is based on a Wiener filter and the filtering is performed on the first portion of each first sound recording. In an alternative embodiment, the adaptive filtering is based on a least square filter.

Prior to the filtering 106, a first noise level of each second sound recording of the second plurality is determined 116, and each first sound recording having a simultaneously recorded second recording with a first noise level above a first determined noise level is discarded 118. The first noise level is based on the variance of the sound level of the complete second sound recording. A first band-pass filtering allowing passage within 60-300 Hz of the complete second sound recording is performed prior to determining the first noise level. Further, first determined noise level is set to 65 dB.

Prior to the filtering 106, a second heart sound level of each first sound recording of the first plurality is also determined 120, and the first sound recordings having a second heart sound level that is below a first determined heart sound level are discarded 122. The second heart sound level is based on the variance of the sound level of the corresponding complete first sound recording. A second band-pass filtering allowing passage within 60-300 Hz of the complete first sound recording is performed prior to determining the first noise level. Further, the first determined heart sound level is set to 60 dB.

Subsequent to the filtering 106 and prior to the determining 107 of an indication for CAD, a second noise level for a second period of each second sound recording is determined 124. Additionally, each first sound recordings having a simultaneously recorded second recording with a second noise level above a second determined noise level is discarded 126. Each second period corresponds in extent to the second portion of the same second sound recording. The second noise level is based on the variance of the sound level of the second period. A third band-pass filtering allowing passage within 100-1200 Hz is performed prior to determining the second noise level. Further, the second determined noise level is set to 60 dB.

Subsequent to the filtering 106 and prior to the determining 107 of an indication for CAD, a third heart sound level for a third period of each first sound recording is determined 128. Further, the first sound recording is discarded 130 if the third heart sound level exceeds a second determined heart sound level. The third period corresponds to first portion of the first sound recording of the corresponding first sound recording. A fourth band-pass filtering allowing passage within 100-1200 Hz is performed prior to determining the third heart sound level. The third heart sound level is based on the variance of the sound levels of the third periods. The determined third heart sound level is set to approximately 3 dB greater than the median of the variance of the sound levels of the third periods.

Figure 5:
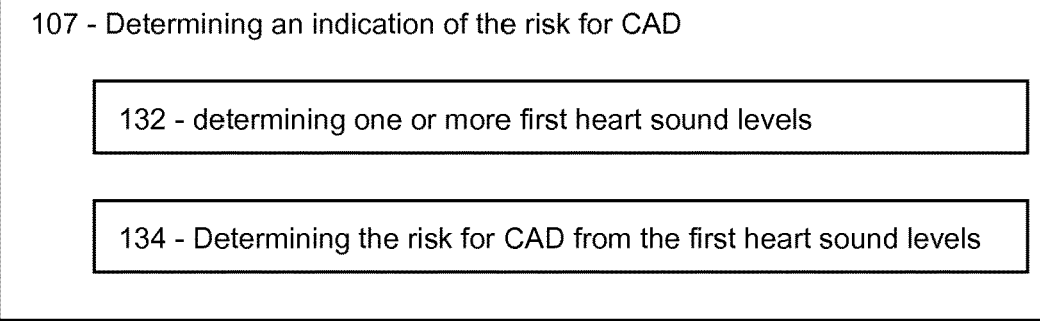
FIG. 5 is a flow chart illustrating a detailed embodiment of the determining an of the indication of the risk for CAD,
FIG. 6 schematically illustrates another embodiment of a system.

FIG. 5 is a flow chart illustrating a detailed embodiment of the determining 107 of the indication of the risk for CAD. This step can be implemented in the above described methods. One or more first heart sound levels from the filtered first sound recordings are determined 132. Each first heart sound level is determined from a first period within a filtered first sound recording. The risk for CAD is then determined 134 based on the one or more first heart sound levels. Each first period correspond in extent to the diastolic period of the corresponding first sound recording.

One example of determining the risk for CAD is to calculate the mean of the one or more first heart sound levels. If the means is greater than a predetermined value, a high risk is indicated, and if the mean is lower than a predetermined value, a low risk is indicated.

Figure 6:
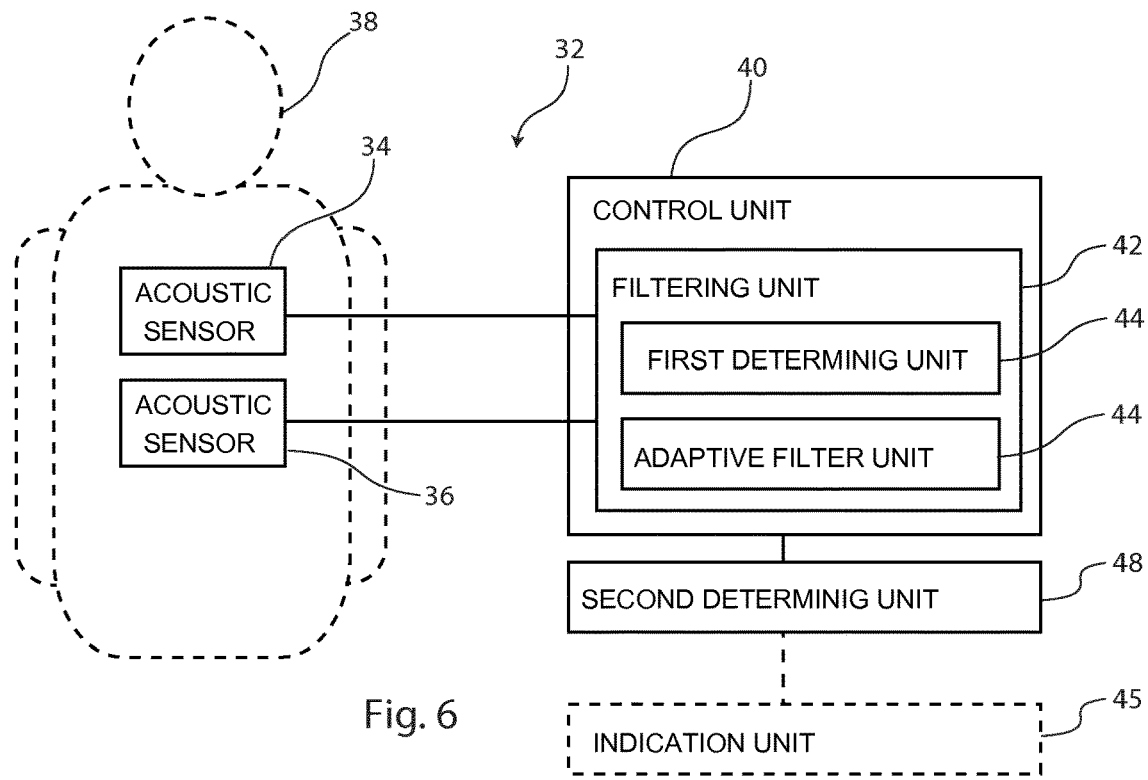

FIG. 6 schematically illustrates another embodiment of a system 32. The system 32 has a first acoustic sensor 34 configured to be placed on the chest of a person 38 and for recording heartbeats, and a second acoustic sensor 36 configured to be placed at the person 38 and for recording ambient background sounds. The system 32 further has a control unit 40 that is operatively connected with the first acoustic sensor 34 and the second acoustic sensor 36.

The control unit 40 can obtain a first plurality of first sound recordings with the first acoustic sensor 34, and each first recording is of a heartbeat of the person 38. Further, the control unit 40 can obtain a second plurality of second sound recording with the second acoustic sensor 36, and each second sound recording is of the ambient background surrounding the person 38 and being recorded simultaneously to a first sound recording of the first plurality.

The control unit 40 has a filtering unit 42 that can perform a filtering of each first sound recording of the first plurality by using a simultaneously recorded second sound recording of the second plurality. The filtering unit 42 has a first determining unit 44 that can determine a diastolic period of the heartbeat of the first sound recording, and an adaptive filter unit 46 that can perform an adaptive filtering of the first sound recording for reducing noise originating from the ambient background that is present in the first sound recording and in the simultaneously recorded second sound recording. The adaptive filtering is based on a first portion of the first sound recording and on a second portion of the simultaneously recorded second sound recording. Additionally, the first portion and the second portion are covered by the diastolic period.

The system 32 further has a second determining unit 48 operatively connected with the control unit 40 unit that can determine an indication of the risk for CAD-based on the filtered first sound recordings of the first plurality. In another embodiment of the system 32, the control unit 40 additionally has an indication unit 45 operatively connected with the second determining unit 48 that can indicate the determined indication. An indication unit 45 can for example have a set of differently colored lamps or a display that shows the determined indication. The indication as such may be color coded or represented by a number that can be associated with the risk for CAD.

Figure 7:
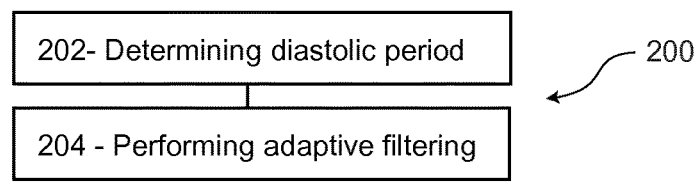
FIG. 7 is a flow chart illustrating a detailed embodiment of a method for filtering.

FIG. 7 is a flow chart illustrating an embodiment of a method 200 that filters a first sound recording of a heartbeat of a person. The filtering is performed by using a second sound recording of the ambient background surrounding the person, where the second sound recording is recorded simultaneously to the first sound recording. A diastolic period of the heartbeat of the first sound recording is first determined 202. Subsequently, an adaptive filtering of the first sound recording is performed 204 for reducing noise originating from the ambient background that is present in the first sound recording and in the second sound recording. The adaptive filtering is based on a first portion of the first sound recording and on a second portion of the second sound recording, and wherein the first portion and the second portion are covered by the diastolic period.

An example embodiment of program code instruction, in this case MATLAB code, for implementing the Wiener filter in the abovementioned embodiments is described below. A filtering function is defined as:

function[$z,Hd$]=Wienerfilter_$c$(noise,$x,M$);

In another embodiment, the filter function is defined as:

function[$z$]=Wienerfilter_$p$(noise,$x,M$);

In the above functions, x is the signal to be denoised, or the first portion of the first sound recording; noise is a vector representing the noise signal, or the second portion of a second sound recording; M is the filter order, z is the filtered signal, or filtered first portion; and Hd are digital filter coefficients. For example, the filter order can be 200 samples corresponding to 25 ms. An autocorrelation matrix of the noise signal is then generated:

$rxx$=xcorr(noise,$M$);

$rxx$=$rxx$($M$+1:end);

$Rxx$=toeplitz($rxx$);

The cross correlation between signal and noise is determined:

$rys$=xcorr($x$,noise,$M$);

$rys$=$rys$($M$+1:end);

Filter coefficient are generated:

$w$=($Rxx$^(−1))*$rys$';

The digital filter coefficients are then generated:

$Hd$=struct('$b$',$w$,'$a$',1);

The noise signal is then generated:

$de$=filter($w$,1,noise);

The noise signal is subtracted from the signal:

$z$=$x$−$de$;

Throughout the specifications, operatively connected may be achieved by or correspond to a wire or wireless connection. Further reference is made to WO 2008/000254 A1, WO2009080040A1, and WO 2012/080209 A1 for performing the steps or providing the features described above.

ITEM LIST

10 diastolic period
12 system
14 first acoustic sensor
16 second acoustic sensor
18 person
20 processor
22 transient memory
24 non-transient memory
25 indicator
26 support
28 housing
32 system
34 first acoustic sensor
36 second acoustic sensor
38 person
40 control unit
42 filtering unit
44 first determining unit
45 indication unit
46 adaptive filter unit
48 first determining unit

The invention claimed is:

1. A method for indicating a risk for coronary artery disease for a person, the method comprising;
    (a) obtaining a first plurality of first sound recordings, wherein each first recording is of a heartbeat of the person,
    (b) obtaining a second plurality of second sound recording, wherein each second sound recording is of an ambient background surrounding the person and being recorded simultaneously to a first sound recording of the first plurality,
    (c) performing a filtering of each first sound recording of the first plurality by using a simultaneously recorded second sound recording of the second plurality, the filtering of each first sound recording comprises:
        (i) determining a diastolic period of the heartbeat of the first sound recording, and
        (ii) determining a first portion of the first sound recording and a second portion of the simultaneously recorded second sound recording, wherein the first portion and the second portion are covered by the diastolic period,
        (iii) determining an adaptive filter for the first sound recording, wherein the adaptive filter is based on the first portion and the second portion and configured for reducing noise originating from the ambient background that is present in both the first sound recording and in the simultaneously recorded second sound recording, and
        (iv) employing the adaptive filter to the first sound recording, and (d) determining an indication of the risk for coronary artery disease based on the filtered first sound recordings of the first plurality.

2. The method according to claim 1, wherein the step (d) of determining an indication comprises:
(d1) determining one or more first heart sound levels from the filtered first sound recordings, wherein each first heart sound level is determined from a first period within a filtered first sound recording, and
(d2) determining the risk for coronary artery disease based on the one or more first heart sound levels.

3. The method according to claim 2, wherein the first period corresponds to a period within the diastolic period.

4. The method according to claim 1, wherein the first portion and the second portion are of equal length and the first portion and the second portion are concurrent.

5. The method according to claim 1, wherein the adaptive filter is based on a Wiener filter and the adaptive filtering may be applied to the first portion of the first sound recording.

6. The method according to claim 1, wherein the method further comprises prior to the step (c) of performing the filtering:
(e) determining a first noise level of each second sound recording of the second plurality, wherein the first noise level is based on a variance of a sound level of the complete second sound recording, and
(f) discarding the first sound recordings having a simultaneously recorded second recording with a first noise level above a first determined noise level, wherein the first determined noise level is approximately 65 dB.

7. The method according to claim 1, wherein the method further comprises prior to the step (c) of performing the filtering:
(g) determining a second heart sound level of each first sound recording of the first plurality, wherein the second heart sound level is based on a mean or variance of a sound level of the complete first sound recording, and
(h) discarding the first sound recordings having a second heart sound level that is below a first determined heart sound level, wherein the first determined heart sound level is approximately 60 dB.

8. The method according to claim 1, wherein the method further comprises subsequent to step (c) of performing the filtering and prior to the step (d) of determining an indication:
(i) determining a second noise level for a second period of each second sound recording of the second plurality, wherein the second period corresponds to the first period and the second noise level is based on a variance of the second period, and
(j) discarding each first sound recordings having a simultaneously recorded second recording with a second noise level in the second period above a second determined noise level, wherein the second determined noise level is approximately 60 dB.

9. The method according to claim 1, wherein the method further comprises subsequent to step (c) of performing the filtering and prior to the step (d) of determining an indication:
(k) determining a third heart sound level for a third period of each first sound recording of the first plurality, wherein the third period corresponds to the first period and the third heart sound level is based on a median of the variance of the sound levels of the third periods, and
(l) discarding the first sound recording if the third heart sound level exceeds a second determined heart sound level, wherein the determined third heart sound level is approximately 3 dB greater than the median of the mean or variance of the sound levels of the third periods.

10. A system for indicating a risk for coronary artery disease for a person, wherein the system comprises;
(A) a first acoustic sensor configured to be placed on the chest of the person and for recording heartbeats,
(B) a second acoustic sensor configured to be placed at the person and for recording ambient background sounds,
(C) a processor operatively connected with the first acoustic sensor and the second acoustic sensor and configured to:
(a) obtain a first plurality of first sound recordings with the first acoustic sensor, wherein each first recording is of a heartbeat of the person,
(b) obtain a second plurality of second sound recording with the second acoustic sensor, wherein each second sound recording is of the ambient background surrounding the person and being recorded simultaneously to a first sound recording of the first plurality,
(c) perform a filtering of each first sound recording of the first plurality by using a simultaneously recorded second sound recording of the second plurality, the filtering of each first sound recording comprises:
(i) determining a diastolic period of the heartbeat of the first sound recording, and
(ii) determining a first portion of the first sound recording and a second portion of the simultaneously recorded second sound recording, wherein the first portion and the second portion are covered by the diastolic period,
(iii) determining an adaptive filter for the first sound recording, wherein the adaptive filter is based on the first portion and the second portion and configured for reducing noise originating from the ambient background that is present in both the first sound recording and in the simultaneously recorded second sound recording, and
(iv) employing the adaptive filter to the first sound recording, and
(d) determining an indication of the risk for coronary artery disease based on the filtered first sound recordings of the first plurality.

11. The system according to claim 10, wherein the system further comprises a support for supporting the first acoustic sensor and the second acoustic sensor and for positioning the second acoustic sensor at the first acoustic sensor.

12. A computer program product for being used in a system comprising: (A) a first acoustic sensor configured to be placed on the chest of a person and for recording heartbeats, (B) a second acoustic sensor configured to be placed at the person and for recording ambient background sounds, and (C) a processor operatively connected with the first acoustic sensor and the second acoustic sensor, the computer program product comprising program code instructions configured to, when executed by the processor of the system, cause the processor to:
(a) obtain a first plurality of first sound recordings with the first acoustic sensor, wherein each first recording is of a heartbeat of the person,
(b) obtain a second plurality of second sound recording with the second acoustic sensor, wherein each second sound recording is of the ambient background surrounding the person and being recorded simultaneously to a first sound recording of the first plurality, (c) perform a filtering of each first sound recording of the first plurality by using a simultaneously recorded second sound recording of the second plurality, the filtering of each first sound recording comprises:
(i) determining a diastolic period of the heartbeat of the first sound recording, and
(ii) determining a first portion of the first sound recording and a second portion of the simultaneously recorded second sound recording, wherein the first portion and the second portion are covered by the diastolic period,
(iii) determining an adaptive filter for the first sound recording, wherein the adaptive filter is based on the first portion and the second portion and configured for reducing noise originating from the ambient background that is present in both the first sound recording and in the simultaneously recorded second sound recording, and
(iv) employing the adaptive filter to the first sound recording, and
(d) determining an indication of the risk for coronary artery disease based on the filtered first sound recordings of the first plurality.

\* \* \* \* \*